United States Patent
Serisier et al.

(10) Patent No.: US 10,835,566 B2
(45) Date of Patent: Nov. 17, 2020

(54) JOINT CARE COMPOSITION

(71) Applicant: MARS, INCORPORATED, McLean, VA (US)

(72) Inventors: Samuel Serisier, Slough (GB); Fanny Comblain, Slough (GB); Yves Henrotin, Slough (GB)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 14/891,120

(22) PCT Filed: May 14, 2014

(86) PCT No.: PCT/EP2014/059850
§ 371 (c)(1),
(2) Date: Nov. 13, 2015

(87) PCT Pub. No.: WO2014/184246
PCT Pub. Date: Nov. 20, 2014

(65) Prior Publication Data
US 2016/0263176 A1  Sep. 15, 2016

(30) Foreign Application Priority Data

May 14, 2013 (EP) .................................... 13305609
May 15, 2013 (EP) .................................... 13305615

(51) Int. Cl.
| | | |
|---|---|---|
| *A61K 36/82* | (2006.01) | |
| *A61K 31/12* | (2006.01) | |
| *A61K 31/401* | (2006.01) | |
| *A61K 38/39* | (2006.01) | |
| *A61K 31/353* | (2006.01) | |
| *A61K 31/198* | (2006.01) | |
| *A23L 33/175* | (2016.01) | |
| *A61K 38/01* | (2006.01) | |
| *A23L 33/105* | (2016.01) | |

(52) U.S. Cl.
CPC ............ *A61K 36/82* (2013.01); *A23L 33/105* (2016.08); *A23L 33/175* (2016.08); *A61K 31/12* (2013.01); *A61K 31/198* (2013.01); *A61K 31/353* (2013.01); *A61K 31/401* (2013.01); *A61K 38/014* (2013.01); *A61K 38/39* (2013.01); *A23V 2002/00* (2013.01)

(58) Field of Classification Search
None
See application file for complete search history.

(56) References Cited

U.S. PATENT DOCUMENTS

| | | |
|---|---|---|
| 2,538,202 A | 1/1951 | Kimball |
| 3,655,406 A | 4/1972 | Klaul |
| 3,922,353 A | 11/1975 | Bernotavicz |
| 4,307,117 A | 12/1981 | Leshik |
| 4,343,823 A | 8/1982 | Todd et al. |
| 4,451,488 A | 5/1984 | Cook et al. |
| 4,546,003 A | 10/1985 | Izzo et al. |
| 4,804,745 A * | 2/1989 | Koepff ................ A61K 38/014 514/16.8 |
| 4,888,187 A | 12/1989 | Given et al. |
| 4,999,205 A | 3/1991 | Todd et al. |
| 5,009,900 A | 4/1991 | Levine et al. |
| 5,077,069 A | 12/1991 | Chang et al. |
| 5,084,293 A | 1/1992 | Todd |
| 5,234,702 A | 8/1993 | Katz et al. |
| 5,266,344 A | 11/1993 | Mimura et al. |
| 5,290,481 A | 3/1994 | Todd |
| 5,290,605 A | 3/1994 | Shapira |
| 5,401,504 A | 3/1995 | Das et al. |
| 5,527,552 A * | 6/1996 | Todd, Jr. .................. A23D 9/06 426/541 |
| 5,643,623 A * | 7/1997 | Schmitz ................. A23G 3/368 426/311 |
| 5,711,961 A | 1/1998 | Reiner et al. |
| 6,034,122 A | 3/2000 | Chayen et al. |
| 6,162,787 A | 12/2000 | Sorgente et al. |
| 6,312,746 B2 * | 11/2001 | Paluch ................... A23K 40/20 426/282 |
| 6,428,817 B1 | 8/2002 | Collin |
| 7,396,912 B2 | 7/2008 | Hsiao et al. |
| 8,937,194 B2 | 1/2015 | Miller |

(Continued)

FOREIGN PATENT DOCUMENTS

| | | |
|---|---|---|
| EP | 0627173 | 12/1994 |
| FR | 2476986 | 9/1981 |

(Continued)

OTHER PUBLICATIONS

Product brochure from NanoString technologies, downloaded Apr. 29, 2017 from http://academicdepartments.musc.edu/cohr/I-cohr/nanostring/humaninflammation.pdf.* S. Snelling, et al. A gene expression study of normal and damaged cartilage in anteromedial gonarthrosis, a phenotype of osteoarthritis. Osteoarthritis and Cartilage 22 (2014) 334-343.*
Ingredients of Kirkland Signature Adult Chicken Dog Food, Downloaded Apr. 28, 2017 from https://www.dogfoodadvisor.com/dog-food-reviews/kirkland-signature-dog-food/.*

(Continued)

*Primary Examiner* — Michael P Cohen
(74) *Attorney, Agent, or Firm* — Mars, Incorporated

(57) ABSTRACT

The present invention relates to a composition comprising curcuminoid with green tea polyphenol or with a combination of glycine, proline and hydroxyproline for use in preventing or treating osteoarthritis. It also relates to a method of preventing or treating osteoarthritis in mammals, the method comprising administering to said mammal a composition which comprises curcuminoid with green tea polyphenol or with a combination of glycine, proline and hydroxyproline.

16 Claims, No Drawings
Specification includes a Sequence Listing.

(56) References Cited

U.S. PATENT DOCUMENTS

| | | | |
|---|---|---|---|
| 2004/0029774 A1* | 2/2004 | Gamay | A61K 9/0056 424/439 |
| 2004/0131728 A1 | 7/2004 | Ootsuka et al. | |
| 2005/0176807 A1 | 8/2005 | Friesen et al. | |
| 2005/0181047 A1 | 8/2005 | Romero | |
| 2006/0062859 A1 | 3/2006 | Blum et al. | |
| 2006/0172012 A1 | 8/2006 | Finley et al. | |
| 2007/0116841 A1* | 5/2007 | Prakash | A23L 2/02 426/548 |
| 2008/0269310 A1 | 10/2008 | Foster | |
| 2008/0317885 A1* | 12/2008 | Baker | A61K 31/192 424/739 |
| 2009/0028840 A1 | 1/2009 | Im et al. | |
| 2012/0052138 A1* | 3/2012 | Park | A61K 36/82 424/729 |
| 2012/0225053 A1 | 9/2012 | Dushenkov et al. | |
| 2017/0196927 A1 | 7/2017 | Serisier | |

FOREIGN PATENT DOCUMENTS

| | | | |
|---|---|---|---|
| JP | S5930057 | 1/1983 | |
| JP | S62220175 | 9/1987 | |
| JP | H0191757 | 4/1989 | |
| JP | 2005232089 | 9/2005 | |
| KR | 20020011594 | 2/2002 | |
| KR | 20040006955 A | 1/2004 | |
| KR | 20120033633 | 4/2012 | |
| WO | 8704602 | 8/1987 | |
| WO | 0074662 | 12/2000 | |
| WO | WO-2007101551 A2 * | 9/2007 | A61K 31/12 |
| WO | 2010106191 | 9/2010 | |
| WO | WO 2012039745 A1 * | 3/2012 | A23K 20/121 |
| WO | 2013132668 | 9/2013 | |

OTHER PUBLICATIONS

Description of Pet Food provided by "The Animal Inn Pet Supplies" (downloaded Mar. 12, 2018 from https://www.theanimalinn.co/which-pet-food. Cited date in Google is Aug. 26, 2010. (Year: 2010).*
Vilai Kuptniratsaikul, et al. Efficacy and Safety of Curcuma domestica Extracts in Patients with Knee Osteoarthritis. The Journal of Alternative and Complementary Medicine, vol. 15, No. 8, 2009, pp. 891-897 (Year: 2009).*
Rashmi Singh, Nahid Akhtar, Tariq M. Haqqi. Green tea polyphenol epigallocatechin-3-gallate: Inflammation and arthritis. Life Sciences 86 (2010) 907-918 (Year: 2010).*
Alfonso Bello and Steffen Oesser. Collagen hydrolysate for the treatment of osteoarthritis and other joint disorders. Current Medical Research and Opinion, vol. 22, No. 11, 2006, 2221-2232. (Year: 2006).*
Preetha Anand,Ajaikumar B. Kunnumakkara,Robert A. Newman,and Bharat B. Aggarwal. Bioavailability of Curcumin: Problems and Promises. Molecular Pharmaceutics, 2007, vol. 4, No. 6, 807-818. (Year: 2007).*
H-H. Sherry Chow, et al. Phase I Pharmacokinetic Study of Tea Polyphenols following Single-dose Administration of Epigallocatechin Gallate and Polyphenon E. Cancer Epidemiology, Biomarkers & Prevention, vol. 10, 53-58, Jan. 2001, pp. 53-58. (Year: 2001).*
Wikipedia entry for "Lecithin", downloaded Aug. 12, 2019 from https://en.wikipedia.org/wiki/Lecithin. (Year: 2019).*
J.D. Lambert, et al. Piperine Enhances the Bioavailability of the Tea Polyphenol (-)-Epigallocatechin-3-gallate in Mice. J. Nutr. 134: 1948-1952, 2004. (Year: 2004).*
G. Shoba, et al. Influence of Piperine on the Pharmacokinetics of Curcumin in Animals and Human Volunteers. Planta Medica 64 (1998) 353-356. (Year: 1998).*
Google Patent Search: lecithin and curcumin Aug. 8, 2019 (Year: 2019).*
Advertisement for Centrum, Lederle Consumer Health, 1993, 1 page.
Advertisement for Choline Cocktail, Twinlab Specialty Corporation, 1994, 1 page.
Advertisement for Oxi-Pro Antioxidant by Champion Nutrition (1993), 1 page.
Booklet for PowerBar, 1993, 5 pages.
Product Information by Quest International on Tumeric Extract 95%, 1 page.
"Medical Poll Reveals 8 Out of 10 Doctors Take an Antioxidant for Food Health", Medical Tribune, 1992, Circle No. 53 of Reader Services Card, 1 page.
"Vitamins", Encyclopedia of Food Science and Technology, parts 4, 6 and 8, vol. 4, John Wiley and Sons, Inc., 1991, pp. 2701-2712; 2718-2727; 2732-2739.
Blumenthal, "Herbs as Traditional Medicine in Canada", American Botanical Council HerbClip, Jan. 12, 1996,.
Cannon, et al., "Acute Phase Response in Exercise. II. Associations Between Vitamin E, Cytokines, and Muscle Proteolysis", The American Physiological Society, 1991, R1235-R1240.
Conney, et al., "Inhibitory Effect of Curcumin and Some Related Dietary Compounds on Tumor Promotion and Arachidonic acid Metabolism in Mouse Skin", Adv. Enz. Reg., 31:385.
Donatus, et al., "Cytotoxic and Cytoprotective Activities of Curcumin", Biochemical Pharmacology, 1990, vol. 39, No. 12, pp. 1869-1875.
Duthie, et al., "Blood Antioxidant Status and Erythrocyte Lipid Peroxidation Following Distance Running", Archives of Biochemistry and Biophysics, 1990, vol. 282, No. 1, pp. 78-83.
Gohil, et al., "Vitamin E Deficiency and Vitamin C Supplements: Exercise and Mitochondrial Oxidation", The American Physiological Society, 1986, pp. 1986-1991.
Halliwell, "Free Radicals and Antioxidants: A Personal View", Nutr. Rev., 52: 253-265, Aug. 1994.
Hasegawa, "Anti-Stress Effect of Beta-Carotene", Ann. N.Y. Acad. Sci.,1993, 691:281-3.
Huang, et al., "Inhibitory Effects of Curcumin on in vitro Lipoxygenase and Cycloxygenase Activities in Mouse Epidermis", Cancer Research, 1991, vol. 51, pp. 813-819.
Huang, et al., "Inhibitory Effects of Curcumin on Tumor Initiation by Benzo[a]pyrene and 7,12-dimethylbenz[a] anthracene", Carcinogenesis, 1992, vol. 13, No. 11, pp. 2183-2186.
Jackson, et al., "Free Radicals and Muscle Damage", British Medical Bulletin, 1993, vol. 49, No. 3, pp. 630-641.
Kinsella, "Dietary Fat and Protaglandins: Possible Beneficial Relationships Between Food Processing adn Public Health", Food Technology, May 1981, pp. 89-98.
Meydani, et al., "Antioxidant Response to Exercise-Induced Oxidative Stress and Protection by Vitamin E", 1992, Ann. N.Y. Acad. Sci., 669:363-364.
Meydani, et al., "Free Radicals, Exercise and Aging", Free Radicals and Aging, (ed. B.P. Yu), CRC Press, London, 2 pages.
Meydani, et al., "Protective Effect of Vitamin E on Exercise-Induced Oxidative Damage in Young and Older Adults", Free Rad. Biol. Med., 1990 , 9 (Suppl 1): R992-R998.
Mukhopadhyay, et al., "Anti-Inflammatory and Irritant Activities of Curcumin Analogues in Rats", Agents and Actions, vol. 12.4, 1982.
Newham, "The Consequences of Eccentric Contractions and Their Relationship to Delayed Onset Muscle Pain", Eur. J. Appl. Physiol., 1988, 57:353-359.
Novelli, et al., "Spin-trappers and Vitamin E Prolong Endurance to Muscle Fatigue in Mice", Free Rad. Biol. Med., 8:9-13, 1990.
Pincemail, et al., "Tocopherol Mobilization During Intensive Exercise", Eur. J. Appl. Physiol., 57:189-191, 1988.
Rabkin, "Why Ibuprofen's Bigger than Aspirin", Hippocrates, Jun. 1994, pp. 20-.
Schmitz, et al., "Analysis of Carotenoids in Human and Animal Tissue", Meth. Enz. 214:102-116, 1993.
Sejersted, et al., "Occupational Muscle Pain and Injury: Scientific Challenges", Eur. J. Appl. Physiol., 57:271-274, 1988.
Singh, "A Current Perspective on Nutrition and Exercise", J. Nutr., vol. 122, pp. 760-765, 1992.

(56) References Cited

OTHER PUBLICATIONS

Smith, "Acute Inflammation: The Underlying Mechanism in Delayed Onset Muscle Soreness", American College of Sports Medicine, vol. 23, No. 5, pp. 542-551, 1990.
Starr, "Inform—Use Supplements to Help Heal Injuries", VeloNews, Aug. 8, 1994, 1 page.
Sumida, et al., "Exercise-Induced Lipid Peroxidation and Leakage of Enzymes Before and After Vitamin E Supplementation", Int. Biochem., 1989, vol. 21, No. 8, pp. 835-838.
Thomas, "Oxidative Stress, Oxidant Defense and Dietary Constituents", Modern Health in Nutrition and Disease (eds M.E. Shils, J.A. Olson and M. Shike), Lea and Febiger, Philadelphia, 1994, pp. 501-512.
Tiidus, et al., "Antioxidant and Oxidative Enzyme Adaptions to Vitamin E Deprivation and Training", Medicine and Science in Sports and Exercise, 1994, vol. 26, No. 3, Abstract.
Toonesen, "Chemistry of Cursumin and Curcuminoids", American Chemical Society, Symposium Series 507, Chapter 11, 1992, 1 page.
Walsh, "The Morning After", Women's Sports & Fitness, 1994, p. 74.
Witt, "Exercise, Oxidative Damage and Effects of Antioxidant Manipulation", J. Nutr., vol. 122, pp. 766-773, 1992.
Ziegler, "A Review of Epidemiologic Evidence that Carotenoids Reduce the Risk of Cancer", J. Nutr., 119P:116-122, Jan. 1989.
Katiyar, et al., "Green tea: a new option for the prevention or control of osteoarthritis", Arthritis Research & Therapy, vol. 13, No. 4, Jan. 1, 2011, p. 121.
"A Balanced Diet", Waltham Book of Dog and Cat Nutrition, Ed. ATB, Edney, Chapter by A. Rainbird, pp. 57-74, Pergamon Press, Oxford, 1988.
"Nutrient Profiles for Dog Foods", Association of American Feed Control Officials Incorporated, pp. 110-119, 1994.
"Nutrient Requirements of Dogs, National Academy Press, Washington DC (ISBN: 0-309-03496-5)", National Research Council, 1985, 7 pgs.
Ahmed, et al., "Green Tea Polyphenol Epigallocatechin-3-Gallate (EGCG) Differentially Inhibits Interleukin-1β-Induced Expression of Matrix Metalloproteinase-1 and -13 in Human Chondrocytes", The Journal of Pharmacology and Experimental Therapeutics, vol. 308, No. 2, Feb. 2004, pp. 767-773.
Ahmed, et al., "Green Tea Polyphenol Epigallocatechin-3-Gallate Inhibits the IL1β-Induced Activity and Expression of Cyclooxygenase-2 and Nitric Oxide Synthase-2 in Human Chondrocytes", Free Radical Biology & Medicine, vol. 33, No. 8, Jun. 27, 2002, pp. 1097-1105.
Clark, et al., "24-Week study on the use of collagen hydrolysate as a dietary supplement in athletes with activity-related joint pain", Current Medical Research and Opinion. vol. 24, No. 5, 1485-1496, Apr. 15, 2008.
Haqqi, et al., "Prevention of collagen-induced arthritis in mice by a polyphenolic fraction from green tea", Proc. Natl. Acad. Sci. USA. vol. 96, pp. 4524-4529, Apr. 1999.
Henrotin, et al., "Chondroitin sulfate in the treatment of osteoarthritis: from in vitro studies to clinical recommendations", Ther Adv Musculoskel Dis. 2(6): 335-348, Dec. 2010.
Kanzaki, et al., "Effect of a dietary supplemental containing glucosamine hydrochloride,chondroitin sulfate and quercetin glycosides on symptomatic knee osteoarthritis: a randomized, double-blind placebo-controlled study", Journal of the Science of Food and Agriculture, 92(4), Oct. 3, 2011, 862-869.
Kelly, "Quercetin", Alternative Medicine Review, Thorne Research Inc., Sandpoint, US, Vo. 16, No. 2, Jun. 1, 2011, 172-194.
Madhan, et al., "Role of green tea polyphenols in the inhibition of collagenolytic activity by collagenase", International Journal of Biologica Macromolecules, 41(1), Mar. 27, 2007, 16-22.
Mereles, et al., "Epigallocatechin-3-gallate (EGCG) for Clinical Trials: More Pitfalls than Promises?", Int. J. Mol. Sci. Aug. 2011, 12, 5592-5603.
Rutter, et al., "Green tea extract suppresses the agerelated increase in collagen crosslinking and fluorescent products in C57BL/6 Mice", Int J Vitam Netr Res, Nov. 2003, 73(6): 453-460.
Watanabe, et al., "Effects of Orally Administreated Functional Foods in Osteoarthrosis", Bio Industry, vol. 28, No. 1, 2011, pp. 28-35.
Zhen, et al., "Inhibition of TGF-β signaling in subchondral bone mesenchymal stem cells attenuates osteoarthritis", Nat Med. Jun. 2013; 19(6): 704-712.
Yin et al., "Research progress on treatment of osteoarthritis using glucosamine, chondroitin sulfate and collagen," Chronic Pathemathol J., Dec. 2013, vol. 14, No. 12, pp. 919-921.
Bello, et al., "Collagen hydrolysate for the treatment of osteoarthritis and other joint disorders: a review of the literature", Current Medical Research and Opinion, vol. 22, No. 11, Sep. 2006, 2221-2232.
Katiyar, et al., "Green tea: a new option for the prevention or control of osteoarthritis", Arthritis Research & Therapy, 2011, 13:121, published Aug. 10, 2011, 7 pages.
Shen, et al., "Dietary polyphenols and mechanisms of osteoarthritis", J. Nutr. Biochem., vol. 23, Nov. 2012, pp. 1367-1377.
TRC, et al., "Efficacy and tolerance of enzymatic hydrolysed collagen (EHC) vs. glucosamine sulphate (GS) in the treatment of knee osteoarthritis (KOA)", International Orthopaedics (SICOT), vol. 35(3), Mar. 2011, pp. 341-348.
Bello, et al., "Collagen Hydrolysate for teh treatment of osteoarthritis and other joint disorders: A review of the literature", Current Medical Research and Opinion, Informa Healthcare, GB, Nov. 1, 2006, vol. 22, No. 11, pp. 2221-2232.
Benito-Ruiz, et al., "A randomized controlled trial on the efficacy and safety of a food ingredient, collagen hydrosylate, for improving joint comfort", International Journal of Food Sciences and Nutrition, Carfax Publishing Ltd. GB, Jan. 1, 2009, vol. 60, No. 2, pp. 99-113.
Santosh, et al., "Green Tea: a new option for the prevention or control of osteoarthritis", Arthritis Research & Therapy, vol. 13, No. 4, Jan. 1, 2011, p. 121.
Toma, et al., "Efficacy and tolerance of enzymatic hydrolyzed collagen (EHC) vs. glucosamine sulphate (GS) in the treatment of knee osteoarthritis (KOA)", International Orthopaedics, Springer, Berlin, Apr. 19, 2010, vol. 35, No. 3, pp. 341-348.

* cited by examiner

SEQUENCE LISTING

<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Bovine HPRT forward primer

<400> SEQUENCE: 1
agtttggaaa tacctggcg                                              19

<210> SEQ ID NO 2
<211> LENGTH: 20
<212> TYPE: DNA
<213> ORGANISM: Artificial Sequence
<220> FEATURE:
<223> OTHER INFORMATION: Bovine HPRT reverse primer

<400> SEQUENCE: 2
agtctttagg ctcgtagtgc                                             20

<210> SEQ ID NO 3
<211> LENGTH: 21
<212> TYPE: DNA
<213> ORGANISM: Artificial Sequence
<220> FEATURE:

<223> OTHER INFORMATION: Bovine interleukin (IL)-6 forward primer

<400> SEQUENCE: 3
tggtgatgac ttctgctttc c                                    21

<210> SEQ ID NO 4
<211> LENGTH: 17
<212> TYPE: DNA
<213> ORGANISM: Artificial Sequence
<220> FEATURE:
<223> OTHER INFORMATION: Bovine interleukin (IL)-6 reverse primer

<400> SEQUENCE: 4
tgccagtgtc tccttgc                                         17

<210> SEQ ID NO 5
<211> LENGTH: 20
<212> TYPE: DNA
<213> ORGANISM: Artificial Sequence
<220> FEATURE:
<223> OTHER INFORMATION: Bovine cyclooxygenase (COX)2 forward primer

<400> SEQUENCE: 5
gtctgatgat gtatgccacc                                      20

<210> SEQ ID NO 6
<211> LENGTH: 22
<212> TYPE: DNA
<213> ORGANISM: Artificial Sequence
<220> FEATURE:
<223> OTHER INFORMATION: Bovine cyclooxygenase (COX)2 reverse primer

<400> SEQUENCE: 6
acgtagtctt caatcacaat ct                                   22

<210> SEQ ID NO 7
<211> LENGTH: 19
<212> TYPE: DNA
<213> ORGANISM: Artificial Sequence
<220> FEATURE:
<223> OTHER INFORMATION: Bovine induced nitric oxide synthase (iNOS)
      forward primer

<400> SEQUENCE: 7
ggcaagcacc acattgaga                                       19

<210> SEQ ID NO 8
<211> LENGTH: 17
<212> TYPE: DNA
<213> ORGANISM: Artificial Sequence
<220> FEATURE:
<223> OTHER INFORMATION: Bovine induced nitric oxide synthase (iNOS)
      reverse primer

<400> SEQUENCE: 8
tgcggctgga tttcgga                                         17

<210> SEQ ID NO 9
<211> LENGTH: 16
<212> TYPE: DNA
<213> ORGANISM: Artificial Sequence
<220> FEATURE:
<223> OTHER INFORMATION: Bovine aggrecans (AGG) forward primer

<400> SEQUENCE: 9
tgcctttgac gtgagc                                          16

<210> SEQ ID NO 10
<211> LENGTH: 19
<212> TYPE: DNA
<213> ORGANISM: Artificial Sequence
<220> FEATURE:
<223> OTHER INFORMATION: Bovine aggrecans (AGG) reverse primer

<400> SEQUENCE: 10
gcattgttgt tgacaaact                                              19

<210> SEQ ID NO 11
<211> LENGTH: 16
<212> TYPE: DNA
<213> ORGANISM: Artificial Sequence
<220> FEATURE:
<223> OTHER INFORMATION: Bovine type II collagen (COL2) forward primer

<400> SEQUENCE: 11
ctgcgtctac cccaac                                                 16

<210> SEQ ID NO 12
<211> LENGTH: 18
<212> TYPE: DNA
<213> ORGANISM: Artificial Sequence
<220> FEATURE:
<223> OTHER INFORMATION: Bovine type II collagen (COL2) reverse primer

<400> SEQUENCE: 12
gggtgcaatg tcaatgat                                               18

<210> SEQ ID NO 13
<211> LENGTH: 25
<212> TYPE: DNA
<213> ORGANISM: Artificial Sequence
<220> FEATURE:
<223> OTHER INFORMATION: Bovine metalloproteinase (MMP)-3 forward primer

<400> SEQUENCE: 13
tctatgaagg agaagctgac ataat                                       25

<210> SEQ ID NO 14
<211> LENGTH: 18
<212> TYPE: DNA
<213> ORGANISM: Artificial Sequence
<220> FEATURE:
<223> OTHER INFORMATION: Bovine metalloproteinase (MMP)-3 reverse primer

<400> SEQUENCE: 14
ttcatgggca gcaacaag                                               18

<210> SEQ ID NO 15
<211> LENGTH: 19
<212> TYPE: DNA
<213> ORGANISM: Artificial Sequence
<220> FEATURE:
<223> OTHER INFORMATION: Bovine A Disintegrin and Metalloproteinase with
      Thrombospondin Motifs (ADAMTS) 4 forward primer

<400> SEQUENCE: 15
ctttcaatgt cccacaggc                                              19

<210> SEQ ID NO 16
<211> LENGTH: 18
<212> TYPE: DNA
<213> ORGANISM: Artificial Sequence

```
<220> FEATURE:
<223> OTHER INFORMATION: Bovine A Disintegrin and Metalloproteinase with
      Thrombospondin Motifs (ADAMTS) 4 reverse primer

<400> SEQUENCE: 16
caggaacgga agcgggta                                                 18

<210> SEQ ID NO 17
<211> LENGTH: 18
<212> TYPE: DNA
<213> ORGANISM: Artificial Sequence
<220> FEATURE:
<223> OTHER INFORMATION: Bovine ADAMTS 5 forward primer

<400> SEQUENCE: 17
gacaccctgg gaatggca                                                 18

<210> SEQ ID NO 18
<211> LENGTH: 20
<212> TYPE: DNA
<213> ORGANISM: Artificial Sequence
<220> FEATURE:
<223> OTHER INFORMATION: Bovine ADAMTS 5 reverse primer

<400> SEQUENCE: 18
cacagaactt ggaatcgtca                                               20
```

JOINT CARE COMPOSITION

The present invention relates to a composition comprising curcuminoid with green tea polyphenol or with a combination of glycine, proline and hydroxyproline for use in preventing or treating osteoarthritis. It also relates to a method of preventing or treating osteoarthritis in mammals, the method comprising administering to said mammal a composition which comprises curcuminoid with green tea polyphenol or with a combination of glycine, proline and hydroxyproline.

Cartilage deterioration can be caused by several reasons such as repeated exercise, instability of the joint, etc., which may result in inflammation of the joints. While a greater portion of humans with arthritis have rheumatoid arthritis, most of the arthritis occurring in companion animals is osteoarthritis.

Nowadays, no cure exists for osteoarthritis, and the pharmacological treatment is limited to alleviating symptoms. The most popular are non-steroidal anti-inflammatory drugs, but these are associated with adverse effects. A safer treatment is desirable.

The first aspect of this invention relates to a composition comprising curcuminoid with green tea polyphenol or with a combination of glycine, proline and hydroxyproline for use in preventing or treating osteoarthritis. Treating osteoarthritis includes ameliorating osteoarthritis symptoms.

The present invention relates, for all aspects, to any mammal, including a human. In particular, the present invention relates to a companion animal such as a dog, a cat or an equine animal (e.g. a horse) or any other such animal that suffers or is prone to suffer from osteoarthritis.

The composition of the present invention comprises curcuminoid. Curcuminoid is curcumin or a derivative of curcumin. The chemical structures of curcuminoids differ in their functional groups.

Curcuminoid includes curcumin, demethoxycurcumin, bis-methoxycurcumin and/or tetrahydrocurcumin.

Curcuminoids are natural phenols that are present, in particular, in the Indian spice turmeric. Turmeric is derived from the roots of the plant *Curcuma longa*. Curcuminoids have also been found in roots of other species in the plant family Zingiberaceae of the *Curcuma* genus. Curcuminoids have a distinctly earthy, bitter, peppery flavour and a mustardy smell.

In particular, turmeric contains 60-80% curcumin, 15-30% demethoxycurcumin and 2-6% bis-demethoxycurcumin.

The curcuminoid in the composition of the invention can be of any format, including a powder or lipid extract.

In some embodiments, curcuminoid can be mixed with phospholipids and/or cellulose, starch or derivatives thereof to form complexes. This may assist in stability and/or to further increase solubility and bioavailability of the curcuminoid.

The curcuminoid can be mixed with essential oils, piperine or bromelain. The curcuminoid can be mixed with phosphatidycholine, for example lecithin.

Preferably, the curcuminoid of the present invention is curcumin, which is the most active curcuminoid. Curcumin according to the present invention includes demethoxycurcumin, bis-demethoxycurcumin and/or tetrahydrocurcumin.

The composition of the invention comprises curcuminoid and green tea polyphenol.

Tea (*Camellia sinensis*), in particular green tea, has a high content of flavonoids, including polyphenols, in particular catechins. Catechins in tea include epigallocatechin-3-gallate (EGCG), epicatechin (EC), epicatechin-3-gallate (ECG), epigallocatechin (EGC), catechin, and gallocatechin (GC).

Preferably, the green tea polyphenols include catechin. Preferably, the catechin includes EGCG. Green tea extract usually contains at least about 25% polyphenols, about 12.5% of catechins and about 9.3% of EGCG.

Epigallocatechin gallate (EGCG) is the ester of epigallocatechin and gallic acid. EGCG is the most abundant catechin in tea and is a potent antioxidant. It is particularly found in green tea. EGCG is a major polyphenol of green tea and exhibits anti-oxidant, anti-tumour and anti-mutagenic activities.

The composition of the invention comprises curcumin and a combination of glycine, proline and hydroxyproline.

A combination of glycine, proline and hydroxyproline represents 50% of the total amino acid content of hydrolyzed collagen. Preferably, a combination of glycine, proline and hydroxyproline is hydrolyzed collagen. The amino acid composition of hydrolyzed collagen is as set in the table below;

TABLE 1

| Amino acids | Percentage |
| --- | --- |
| Proline/Hydroxyproline | 25% |
| Glycine | 20% |
| Glutamic acid | 11% |
| Arginine | 8% |
| Alanine | 8% |
| Other essential amino acids | 16% |
| Other non-essential amino acids | 12% |

Hydrolyzed collagen is obtained by the enzymatic hydrolysis of collagenous tissues found in the bones, skin, and connective tissue of animals such as cattle, fish, horses, pigs, and rabbits. Hydrolyzed collagen is well digested and is preferentially accumulated in cartilage.

A preferred composition includes curcuminoid, green tea polyphenol and a combination of glycine, proline and hydroxyproline. Preferably, this composition includes curcumin, green tea polyphenol and hydrolyzed collagen.

The invention is preferably a foodstuff. It can be any foodstuff, such as dry, semi moist or wet food product. In particular, the foodstuff may be a pet food product.

The pet foodstuff is preferably a commercial pet food product. Such a product is preferably sold as a product for feeding to a pet animal, in particular a pet cat or a pet dog.

A typical pet foodstuff contains about 20-30% crude protein and about 10-20% fat, the remainder being carbohydrate, including dietary fibre and ash. A typical wet or moist product contains (on a dry matter basis) about 40% fat, 50% protein and the remainder being fibre and ash. The foodstuff of the invention may be a dry product (with approximately 5 to approximately 15% moisture), a semi-moist product (with approximately 15 to approximately 70% moisture) or a wet product (with approximately 70 to approximately 90% moisture).

The remaining components of the foodstuff are not essential to the invention and typical standard products can be included. The combined ingredients of the foodstuff according to the invention can provide all of the recommended vitamins and minerals for the particular animal in question (a complete and balanced food).

The foodstuff according to the present invention encompasses any product which a pet consumes in its diet. Thus, the invention covers standard food products including liquids, as well as pet food snacks (for example, snack bars, pet chew, crunchy treat, cereal bars, snacks, biscuits and sweet products) and supplements.

The foodstuff can be provided as a food supplement. The food supplement can be a powder, sauce, topping, biscuit, kibble, pocket or tablet that can be administered with or without an additional foodstuff. Where the food supplement is administered with an additional foodstuff, the food supplement can be administered sequentially simultaneously or separately. The food supplement may be mixed with the foodstuff, sprinkled over the foodstuff or served separately. Alternatively, the food supplement can be added to a liquid provided for drinking such as water or milk.

The foodstuff is preferably a cooked product. It may incorporate meat or animal derived material (such as beef, chicken, turkey, lamb, fish, blood plasma, marrow bone etc. or one or more thereof). The product alternatively may be meat free (preferably including a meat substitute such as soya, maize gluten or a soya product) in order to provide a protein source. The foodstuff may contain additional protein sources such as soya protein concentrate, milk proteins, gluten etc. The foodstuff may also contain a starch source such as one or more grains (e.g. wheat, corn, rice, oats, barley etc.), or may be starch free.

The foodstuff of the invention is preferably produced as a dry product containing from approximately 5% to approximately 15% moisture. The preferred dry food is more preferably presented as a small biscuit—like kibbles.

The table below details the amount of the composition according the present invention and the amount of the composition for the dogs to take according to the present invention:

When the diet is dry the "as is" weight is the same as the "dry matter weight".

Preferably, the amount of curcuminoid in the composition ranges from about 0.01 to 0.07% (as is) (14 to 46 mg/400 kcal). Most preferably, the amount of curcuminoid is 0.035% (as is) (36 mg/400 kcal).

In some embodiments, the curcuminoid in the composition is curcumin at an amount ranging from about 0.005 to 0.15% by weight of curcumin on an "as is" weight percent of the food. The amount of curcumin can be any amount from 0.005 to 0.15% (as is) (7 to 99 mg/400 kcal). Preferably, the amount of curcumin ranges from about 0.01 to 0.05% (as is) (14 to 32 mg/400 kcal). Most preferably, the amount of curcumin is 0.026% (as is) (27 mg/400 kcal).

The composition in the first aspect of the invention may comprise green tea polyphenol in an amount ranging from about 0.01 to 1.1% by weight of green tea polyphenol on an "as is" weight percent of the food. The amount of green tea polyphenol can be any amount from 0.01 to 1.1% (as is). The amount of green tea polyphenol can be any amount from 0.1 to 1% (as is). The amount of green tea polyphenol can be any amount from 0.1 to 0.6% (as is). The amount of green tea polyphenol can be any amount from 0.3 to 0.6% (as is).

The composition in the first aspect of the invention may comprise green tea polyphenol in an amount ranging from about 0.01 to 0.3% by weight of green tea polyphenol on an "as is" weight percent of the food. The amount of green tea polyphenol can be any amount from 0.01 to 0.3% (as is) (14 to 197 mg/400 kcal). Preferably, the amount of green tea polyphenol ranges from about 0.03 to 0.17% (as is) (43 to 113 mg/400 kcal). Most preferably, the amount of green tea polyphenol is 0.085% (as is) (87 mg/400 kcal).

TABLE 2

|  | Diet 1 | Diet 2 | Diet 3 | Energy need (kcal/kg 0.75) | | |
| --- | --- | --- | --- | --- | --- | --- |
|  | 3515 kcal % DM | 2500 kcal % DM | 5600 kcal % DM | 80 mg/400 kcal | 95 mg/400 kcal | 145 mg/400 kcal |
| Curcuma (turmeric) extract | 0.171 | 0.07 | 0.32 | 210 | 175 | 102 |
| Curcuminoids | 0.034 | 0.013 | 0.065 | 43 | 35 | 22 |
| Curcumin | 0.026 | 0.01 | 0.05 | 33 | 27 | 15 |
| Green tea extract | 0.341 | 0.155 | 0.63 | 414 | 349 | 225 |
| Green tea poly | 0.085 | 0.035 | 0.16 | 106 | 87 | 51 |
| Green tea EGCG | 0.032 | 0.01 | 0.06 | 39 | 32 | 15 |
| Collagen hydrolyzed | 1.706 | 0.7 | 3.2 | 2108 | 1747 | 1016 |
| Glycine | 1.158 | 0.53 | 2.15 | 1416 | 1185 | 767 |
| Proline | 1.358 | 0.63 | 2.5 | 1651 | 1390 | 911 |
| Hydroxyproline | 0.177 | 0.08 | 0.33 | 217 | 182 | 116 |
| Total gly + pro + hydroxypro | 2.693 | 1.2 | 5 | 3295 | 2757 | 1736 |

The composition in the first aspect of the invention may comprise curcuminoid at an amount ranging from about 0.005 to 1.1% by weight of curcuminoid on an "as is" weight percent of the food. The amount of curcuminoid can be any amount from 0.005 to 1.1% (as is). The amount of curcuminoid can be any amount from 0.1 to 1% (as is). The amount of curcuminoid can be any amount from 0.1 to 0.6% (as is). The amount of curcuminoid can be any amount from 0.3 to 0.6% (as is).

The composition in the first aspect of the invention may comprise curcuminoid at an amount ranging from about 0.005 to 0.15% by weight of curcuminoid on an "as is" weight percent of the food. The amount of curcuminoid can be any amount from 0.005 to 0.15% (as is) (7 to 99 mg/400 kcal).

In some embodiments, the green tea polyphenol is EGCG at an amount ranging from about 0.005 to 0.2% by weight of EGCG on an "as is" weight percent of the food (7 to 131 mg/400 kcal). The amount of EGCG can be any amount from 0.01 to 0.06% (as is) (14 to 39 mg/400 kcal). Most preferably, the amount of EGCG is 0.032% (as is) (33 mg/400 kcal).

The composition in the first aspect of the invention may comprise a combination of glycine, proline and hydroxyproline in an amount ranging from about 0.5 to 10% by weight of combined glycine, proline and hydroxyproline on an "as is" weight percent of the food. The amount of combined glycine, proline and hydroxyproline can be any amount from 0.5 to 10% (as is) (720 to 6591 mg/400 kcal).

Preferably, the amount of combined glycine, proline and hydroxyproline ranges from about 1.2 to 5% (as is) (1736 to 3295 mg/400 kcal). Most preferably, the amount of combined glycine, proline and hydroxyproline is 2.7% (as is) (2780 mg/400 kcal).

In some embodiment, the combination of glycine, proline and hydroxyproline is hydrolyzed collagen in an amount ranging from about 0.5 to 5% by weight of combined glycine, proline and hydroxyproline on an "as is" weight percent of the food. The amount of hydrolyzed collagen can be any amount from 0.5 to 5% (as is) (720 to 3295 mg/400 kcal). Preferably, the amount of hydrolyzed collagen ranges from about 0.7 to 3.2% (as is) (1016 to 2138 mg/400 kcal). Most preferably, the amount of hydrolyzed collagen is 1.7% (as is) (1750 mg/400 kcal).

In other embodiments, the composition may comprise curcumin in an amount of about 27 mg/400 kcal (35 mg/400 kcal of curcuminoids) with about 87 mg/400 kcal of green tea polyphenol and with about 2757 mg/400 kcal of combined glycine, proline and hydroxyproline, wherein the combination of glycine, proline and hydroxyproline is hydrolyzed collagen. Preferably, wherein the combination of glycine, proline and hydroxyproline is hydrolyzed collagen and is present in the composition at an amount of about 1747 mg/400 kcal.

In other embodiments, the composition may comprise curcumin in an amount of about 33 mg/400 kcal (43 mg/400 kcal of curcuminoids) with about 106 mg/400 kcal of green tea polyphenol and with about 3295 mg/400 kcal of combined glycine, proline and hydroxyproline, wherein the combination of glycine, proline and hydroxyproline is hydrolyzed collagen. Preferably, wherein the combination of glycine, proline and hydroxyproline is hydrolyzed collagen and is present in the composition at an amount of about 2108 mg/400 kcal.

In other embodiments, the composition may comprise curcumin in an amount of about 15 mg/400 kcal (22 mg/400 kcal of curcuminoids) with about 51 mg/400 kcal of green tea polyphenol and with about 1736 mg/400 kcal of combined glycine, proline and hydroxyproline, wherein the combination of glycine, proline and hydroxyproline is hydrolyzed collagen. Preferably, wherein the combination of glycine, proline and hydroxyproline is hydrolyzed collagen and is present in the composition at an amount of about 1016 mg/400 kcal.

These values apply to a composition for feeding to a mammal, in particular a companion animal.

The second aspect of the invention relates to a method of preventing or treating osteoarthritis in mammals.

Osteoarthritis (OA) is a degenerative and inflammatory condition that affects the joints in mammals. It is also known as degenerative arthritis or degenerative joint disease. Osteoarthritis is a group of abnormalities involving degradation of joints, including articular cartilage and sub-chondral bone.

Osteoarthritis is the consequence of an imbalance of catabolism and anabolism, wherein catabolism is increased; anabolism is decreased causing the inflammation of chondrocytes. Chondrocytes are the only cells found in healthy cartilage. They produce and maintain the cartilaginous matrix, which consists mainl The present invention relates, for all aspects, to any mammal, including a human. In particular the present inveny of collagen and proteoglycans. The composition of the invention has demonstrated to provide, inter alia, a decrease in inflammation, a decrease in catabolism and an increase in anabolism in in vitro inflammation-induced chondrocytes and in in vitro healthy chondrocytes. Thus, the composition of the invention prevents and/or treats osteoarthritis in animals.

tion relates to a companion animal such as a dog, a cat or an equine animal (e.g. a horse) or any other such animal that suffers or is prone to suffer from osteoarthritis.

In particular, it is a desire in the area of pet foodstuff and companion animal health to provide foodstuff including supplements suitable to support the health of the companion animals. In particular, it is desire to provide diets suitable to promote or maintain the health of already healthy companion animals.

In particular, the second aspect of the invention provides a method for preventing and treating osteoarthritis in mammals, including ameliorating the symptoms of osteoarthritis, in particular companion animals. The method comprises administering to said animal a composition which comprises curcumin with green tea polyphenol or with a combination of glycine, proline and hydroxyproline. The animal may be in need thereof. Since a significant number of dogs suffer from osteoarthritis in their lifetime, all dogs can be considered as in need of prevention.

In particular embodiments, the method comprises administering to said animal a composition comprising curcumin, green tea polyphenol and a combination of glycine, proline and hydroxyproline. Most preferably, the combination of glycine, proline and hydroxyproline is hydrolysed collagen.

Further, the method is preferably administered to an animal, in particular a companion animal, that suffers from osteoarthritis and is in need of ameliorating the symptoms of osteoarthritis or in need of preventing further symptoms of osteoarthritis or in need of treatment of osteoarthritis. This may be to, for example a young pet animal, such as a puppy, or an older companion animal. Where the composition is a foodstuff, the foodstuff may be administered in a dietary regime in accordance with the usual dietary regime of the companion animal. The foodstuff may comprise 100% of the diet of the companion animal or a lesser proportion, depending on the level of prevention or treatment required. The foodstuff allows the composition to be administered with ease thus avoiding a need to supplement the companion animal's food. In addition, the foodstuff can be administered by the animal's owner thus avoiding constant veterinary supervision. The foodstuff may be available at any outlet selling pet food products or may be available from a veterinarian. The foodstuff may be as described above according to the first aspect of the invention.

As used herein, the term "administration" also includes feeding or any other method of oral administration. Other means of administration may include tablets, capsules, injection, suppositories or any other suitable means.

Preferred features for the second aspect of the invention apply as for the first aspect mutatis mutandis.

The present description includes a method for preparing the composition of the first aspect of the invention.

The foodstuff can be made according to any method known in the art such as in Waltham Book of Dog and Cat Nutrition, Ed. ATB Edney, Chapter by A. Rainbird, entitled "A Balanced Diet" in pages 57 to 74 Pergamon Press Oxford.

For example, a process for the manufacture of a foodstuff as defined herein comprises mixing together ingredients with the composition comprising curcuminoid with green tea polyphenol or with a combination of glycine, proline and hydroxyproline and forming a foodstuff, in particular a pet foodstuff. Heating/cooking may be applied to any one or more of the ingredients prior to, during or following the mixing.

The composition can be sprayed onto the foodstuff, mixed in with the foodstuff or incorporated into the foodstuff in a matrix. Methods of inclusion of the composition are known in the art.

The importance of the present invention is the beneficial properties of curcuminoid with either green tea polyphenol or with a combination of glycine, proline and hydroxyproline (optionally as hydrolyzed collagen). In particular, an effect which is more than the cumulative effect is seen.

A further benefit is seen with the triple combination of ingredients of: curcuminoid, green tea polyphenol and glycine, proline and hydroxyproline (optionally as hydrolyzed collagen).

The combination of the compounds of the composition of the present invention can provide a synergistic effect in terms of one or more of decreasing inflammation, decreasing catabolism and increasing anabolism.

The invention will now be further described by way of reference to the following Examples, which are provided for the purpose of illustration only and are not to be construed as being limiting on the invention.

EXAMPLE 1

Individual Screening of Compounds

Experiments were carried out to assess the effect of several compounds on primary culture of bovine chondrocytes, in which inflammatory and catabolic processes are induced by interleukin-1 beta to mimic the effect of arthritic chondrocytes.

The table below details the biomarkers that were measured throughout the experiments to show the effect of the compounds of the three metabolic pathways on chondrocytes.

TABLE 3

Biomarkers tested

| Biomarkers produced by chondrocytes | Inflammation | NO |
| --- | --- | --- |
|  |  | PGE2 |
| Genes expressed by chondrocytes |  | IL-6 |
|  |  | COX2 |
|  |  | iNOS |
|  | Catabolism | MMP3 |
|  |  | ADAMTS4 |
|  |  | ADAMTS5 |
|  | Anabolism | COL2 |
|  |  | AGG |

Primary Culture of Bovine Chondrocytes in Monolayer

Normal bovine articular cartilage was obtained from the metacarpal-phalangeal joint of 1 to 2 year old steers shortly after death. Full-depth articular cartilage was excised and immersed in Dulbecco's Modified Eagle Medium (DMEM) (with phenol red and 4.5 g/L glucose) supplemented with N-(2-hydroxyethyl)piperazine-N'-(2-ethanesulfonic acid) (HEPES) 10 mM, penicillin (100 U/ml) and streptomycin (0.1 mg/ml) (all from Lonza, Verviers, Belgium). After three washings, chondrocytes were released from cartilage by sequential enzymatic digestions with 0.5 mg/ml hyaluronidase type IV S (Sigma-Aldrich, Bornem, Belgium) for 30 min at 37° C., 1 mg/ml pronase E (Merck, Leuven, Belgium) for 1 h at 37° C. and 0.5 mg/ml clostridial collagenase IA (Sigma-Aldrich, Bornem, Belgium) for 16 to 20 h at 37° C. The enzymatically isolated cells were then filtered through a nylon mesh (70 μm), washed three times, counted and filled to the density of 0.25×106 cells/ml of DMEM (with phenol red and 4.5 g/L glucose) supplemented with 10% foetal bovine serum, 10 mM HEPES, 100 U/ml penicillin, 0.1 mg/ml streptomycin, 2 mM glutamine (all from Lonza, Verviers, Belgium) and 20 μg/ml proline (Sigma-Aldrich, Bornem, Belgium). Cells were seeded in a 6-well plate at 0.5×106 cells/well by adding 2 ml of the previously described culture medium/well and cultured in monolayer for 5 days. Chondrocytes were then cultured in monolayer until confluence (for about 2 days) in DMEM (phenol red-free and containing only 1 g/L glucose) (Lonza, Verviers, Belgium) supplemented with 1% fetal bovine serum, 10 mM HEPES, 100 U/ml penicillin, 0.1 mg/ml streptomycin, 2 mM glutamine and 20 μg/ml proline. Only primary cultures were used to ensure the stability of chondrocyte phenotype.

When cells achieved confluence, the culture medium was removed and replaced by fresh culture medium (DMEM phenol red-free and containing only 1 g/L glucose supplemented with 1% fetal bovine serum, 10 mM HEPES, 100 U/ml penicillin, 0.1 mg/ml streptomycin, 2 mM glutamine and 20 μg/ml proline) containing some nutraceuticals (12.5 μg/ml of each of them) and in the absence or in the presence of recombinant porcine IL-1β ($10^{-11}$ M) (RD System, Abingdon, UK).

The anti-inflammatory power of the compounds (firstly individually and then in combination) was tested by measuring the chondrocyte viability and the production of PGE2 and NO.

The compounds were added in the culture medium either before inflammation (prevention effect measurement), either simultaneously of the inflammation (treatment effect measurement).

List of Compounds Screened:
1) Fish oil: 18% EPA+10% DHA (DSM)
2) EPA 99% (Sigma):
3) DHA 99% (Sigma):
4) Aloe Vera (Naturex)
5) Nettle leaf extract (Naturex)
6) Resvida: 99% Resveratrol (DSM)
7) Green tea extract: 25% polyphenols of which 12.5% are catéchines and 8% is EGCG: (Naturex)
8) Pine bark extract: Pycnogenol: 65-75% procyanidines (Biolandes)
9) Premix of vitamins including vitamin D3
10) GLM (AromaNZ)
11) collagen hydrolysate (Fortigel de Gelita [3.3 kDa]: hydrolyzed pork collagen)
12) ASU (Sochim)
13) *Curcuma* powder: 85% curcuminoids (Naturex)

The results showed the 3 compounds to use were *curcuma* extract, hydrolysate collagen and green tea extract, which showed significant effects on different parameters. After that, these 3 compounds were tested in response-dose.

EXAMPLE 2

Dose Responses

The methodology of example 1 was followed. Four different concentrations were tested to cover the range of concentrations corresponding to $10^{-5}$ M, depending on the molecular weight: 0.5 μg/ml, 2.5 μg/ml, 12.5 μg/ml and 62.5 μg/ml.

The results showed that the concentration which gave the best effects without giving toxic effects was 12.5 μg/ml for each compound. This is why the concentration of 12.5 μg/ml was used for testing compounds in combination with each other.

EXAMPLE 3

Testing Particular Combinations of the Compounds and the Synergistic Effects

The method of example 1 was followed.
Supplementation with Compounds
When cells achieved confluence, the culture medium was removed and replaced by fresh culture medium (DMEM phenol red-free and containing only 1 g/L glucose supplemented with 1% fetal bovine serum, 10 mM HEPES, 100 U/ml penicillin, 0.1 mg/ml streptomycin, 2 mM glutamine and 20 µg/ml proline) containing some compounds (12.5 µg/ml of each of them) and in the absence or in the presence of recombinant porcine IL-1β ($10^{-11}$ M) (RD System, Abingdon, UK).

The three compounds were tested namely, curcuma extract (Naturex, Avignon, France), hydrolysate collagen (Gelita, Eberbach, Germany) and green tea extract (Naturex, Avignon, France). Curcuma extract was prepared as a 12.5 mg/ml solution in tetrahydrofuran (Merck, Leuven, Belgium) and then further diluted 1000 times in cell culture medium. Hydrolysate collagen and green tea extract were dissolved in water at the concentration of 12.5 mg/ml, filtered through a sterile mesh (0.20 µm) and then further diluted 1000 times in cell culture medium. The compounds were tested alone at the final concentration of 12.5 µg/ml or in combination (12.5 µg/ml curcuma extract+12.5 µg/ml hydrolysate collagen; 12.5 µg/ml curcuma extract+12.5 µg/ml green tea extract; 12.5 µg/ml curcuma extract+12.5 µg/ml hydrolysate collagen+12.5 µg/ml green tea extract) in the absence or in the presence of recombinant porcine IL-1β ($10^{-11}$ M). The effects of the compounds were compared to controls: DMEM alone or DMEM+IL-1β.

Culture Stop

After 24 h in these conditions, conditioned culture medium of three wells of each condition was collected and stored at −20° C. The cells of these corresponding wells were scraped, an RNA extraction was made using RNeasy mini kit (Qiagen, Venlo, Netherlands), a reverse transcriptase polymerase chain reaction was realized and then a quantitative real time polymerase chain reaction was realized, using the LightCycler 480 (Roche, Vilvoorde, Belgium) to analyze gene expression.

After 48 h in these conditions, conditioned culture medium of the remaining wells (3 of each condition) was collected (lactate dehydrogenase release assay) and stored at −20° C. until analysis (nitrite and prostaglandin E2 assays). Cells were scraped and homogenized in 500 µl of Tris-HCl buffer by ultrasonic dissociation for 20 s at 4° C., to measure DNA content.

Lactate Dehydrogenase Release Assay

Cell viability was estimated by quantifying the release of lactate dehydrogenase (LDH) in the culture supernatant. A 100 µl sample of the supernatant or dilutions of standard solution (LDH from rabbit muscle) was mixed with 50 µl of Tris buffer (10 mM Tris-HCl (pH 8.5), 0.1% bovine serum albumin) containing 800 mM lactate. Then, 50 µl of colorimetric reagent, 1.6 mg/ml iodonitrotetrazolium chloride (Sigma-Aldrich, Bornem, Belgium), 4 mg/ml nicotinamide adenine dinucleotide (Roche Diagnostics, Brussels, Belgium), and 0.4 mg/ml phenazine methosulfate (Sigma-Aldrich, Bornem, Belgium) were added, and the absorbance at 492 nm was read after 10 min of incubation at room temperature.

DNA Assay

Chondrocytes were homogenized in 500 µl of Tris-HCl buffer by ultrasonic dissociation for 15 s at 4° C. DNA content was measured in the cell extracts using the fluorimetric method of Hoechst.

Nitrite Assay

Nitric oxide (NO) production was determined by quantifying its derived product, nitrite, in the culture supernatant using a spectrophotometric method based upon the Griess reaction. Briefly, 100 µl of the supernatant or sodium nitrite (NaNO2) standard dilutions were mixed with 100 µl of Griess reagent (0.5% sulphanilamide, 0.05% naphtyl ethylene diamine dihydrochloride, 2.5% H3PO4). The absorption was measured at 540 nm. The production of NO was expressed per microgram of DNA.

PGE2 Assay

Prostaglandin E2 (PGE2) production was measured in the culture supernatant using the DetectX PGE2 High Sensitivity Immunoassay kit (Arbor Assays, Mich., USA). Briefly, 100 µl of the supernatant or PGE2 standard dilutions were pipetted into a clear microtiter plate coated with an antibody to capture mouse IgG. A PGE2-peroxidase conjugate (25 µl) is added to the standards and supernatants in the wells. The binding reaction is initiated by the addition of 25 µl of a monoclonal antibody to PGE2. After an overnight incubation at 4° C., the plate is washed and 100 µl of substrate is added. The substrate reacts with the bound PGE2-peroxidase conjugate. After a short incubation, the reaction is stopped and the intensity of the generated colour is detected at 450 nm wavelength. The production of PGE2 was expressed per microgram of DNA.

Quantitative Real-Time Reverse Transcriptase Polymerase Chain Reaction (RT PCR)

RNA from cells from 3 wells of each condition was isolated using RNeasy mini kit (Qiagen, Venlo, Netherlands). Then, RNA was reverse transcribed. Quantitative real time Polymerase Chain Reaction (PCR) was performed by using the SYBR Premix Ex Taq (Tli RNaseH Plus) (Westburg, Leusden, Netherlands). The PCR template source was either first-strand cDNA or purified DNA standard. Primer sequences used to amplify the desired cDNA were as follows: bovine HPRT forward and reverse primers: 5'-AGTTTGGAAATACCTGGCG-3' and 5'-AGTCTTTAGGCTCGTAGTGC-3'; bovine interleukin (IL)-6 forward and reverse primers: 5'-TGGTGATGACTTCTGCTTTCC-3' and 5'-TGCCAGTGTCTCCTTGC-3'; bovine cyclooxygenase (COX)2 forward and reverse primers: 5'-GTCTGATGATGTATGCCACC-3' and 5'-ACGTAGTCTTCAATCACAATCT-3'; bovine induced nitric oxide synthase (iNOS) forward and reverse primers: 5'-GGCAAGCACCACATTGAGA-3' and 5'-TGCGGCTGGATTTCGGA-3'; bovine aggrecans (AGG) forward and reverse primers: 5'-TGCCTTTGACGTGAGC-3' and 5'-GCATTGTTGTTGACAAACT-3'; bovine type II collagen (COL2) forward and reverse primers: 5'-CTGCGTCTACCCCAAC-3' and 5'-GGGTGCAATGTCAATGAT-3'; bovine metalloproteinase (MMP)-3 forward and reverse primers: 5'-TCTATGAAGGAGAAGCTGACATAAT-3' and 5'-TTCATGGGCAGCAACAAG-3'; bovine A Disintegrin and Metalloproteinase with Thrombospondin Motifs (ADAMTS) 4 forward and reverse primers: 5'-CTTTCAATGTCCCACAGGC-3' and 5'-CAGGAACGGAAGCGGGTA-3'; bovine ADAMTS 5 forward and reverse primers: 5'-GACACCCTGGGAATGGCA-3' and 5'-CACAGAACTTGGAATCGTCA-3'.

Amplification was performed with a spectrofluorometric thermal cycler (LightCycler 480, Roche Diagnostics, Vilvoorde, Belgium). To standardize mRNA levels, we amplified HPRT, a housekeeping gene, as an internal control. Gene expression was normalized by calculating the ratio between the number of cDNA copies of IL-6, COX2, iNOS, AGG, COL2, MMP-3, ADAMTS4, ADAMTS5, and that of HPRT.

Results were expressed as the mean percentage of increase compared to the control. Statistical significance was assessed using the t-test. Differences were considered statistically significant at $p<0.05$. Table below details the results provided when combining the compounds and the synergistic effects observed.

TABLE 4

|  |  |  | Control | Curcumin (=C) | Hydrolyzed collagen (=O) | Green tea (=T) | CO | CT | COT |
|---|---|---|---|---|---|---|---|---|---|
| Chondrocyte produced biomarkers | Inflammation | NO | 0 | 0 | 0 | 0 | 0 | 0 | 0 |
|  |  | NO + IL1B | 100 | −96* | 23** | −14* | −100*** | −100* | −100*** |
|  |  | PGE2 | 0 | 0 | 0 | 0 | 0 | 0 | 0 |
|  |  | PGE2 + IL1B | 100 | −99* | 1** | 363** | −100* | −100*** | −100*** |
| Genes expressed by chondrocytes |  | IL-6 | 100 | −82* | 307** | 252** | −43* | −38* | −65* |
|  |  | IL-6 + IL1B | 100 | −84* | −1* | −8* | −89* | −100* | −99* |
|  |  | COX2 | 100 | 49** | 54** | 86** | 378** | 84** | 27** |
|  |  | COX2 + IL1B | 100 | −51* | −24* | −26* | −58* | −87* | −92* |
|  |  | iNOS | 100 | −76* | 123** | 207** | −65*** | −27*** | −25*** |
|  |  | iNOS + IL1B | 100 | −86* | −13* | 15** | −91* | −96* | −97* |
|  | Catabolism | MMP3 | 100 | 40** | 109** | 161** | 91* | −10*** | −15*** |
|  |  | MMP3 + IL1B | 100 | −58* | −20* | −22* | −85* | −99* | −99* |
|  |  | ADAMTS4 | 100 | −21* | 12** | 9** | 16** | −14* | −58*** |
|  |  | ADAMTS4 + IL1B | 100 | −55* | −23* | −28* | −68* | −83* | −84* |
|  |  | ADAMTS5 | 100 | −16* | 2** | 32** | −31*** | −28*** | −41*** |
|  |  | ADAMTS5 + IL1B | 100 | −47* | −13* | 22** | −52* | −76*** | −71*** |
|  | Anabolism | COL2 | 100 | −77** | 13* | 18* | −84** | −62** | −74** |
|  |  | COL2 + IL1B | 100 | −57** | −2** | 55* | −67** | 29*** | 67*** |
|  |  | AGG | 100 | −77** | 54** | 33* | −78** | −30** | −53** |
|  |  | AGG + IL1B | 100 | −77** | −4** | 123* | −82** | 186*** | 337*** |

(*Beneficial effect; Negative effect; *More beneficial than expected)

DISCUSSION

The results of the combinations were better than the additive effect of each compound. An explanation is that because compounds act on different metabolic ways which are related, when there is inflammation, catabolism increases and anabolism decreases. Thus, our non-limiting hypothesis is that curcumin inhibits inflammation induced by IL-1β (and also induced by collagen and green tea). Once the inflammation is inhibited, catabolism decreases and collagen and green tea polyphenols can have their positive effect on anabolism. Given arthrosis is a vicious circle (inflammation induces catabolism which induces inflammation, etc), when catabolism decreases (and anabolism increases), there is a decrease of inflammation and we recover a virtuous circle.

Moreover, in general, in healthy cells there is always a balance between catabolism and anabolism. We saw that the combinations could have positive effects on the metabolism of healthy cells (with no induction of inflammation by IL-1β). It is very interesting because, in case of arthrosis or before arthrosis, cells which are still in good health can be protected by our combinations.

The invention claimed is:

1. A joint care composition comprising curcuminoid, green tea polyphenol, and hydrolyzed collagen, wherein the combination of curcuminoid, green tea polyphenol, and hydrolyzed collagen provides a synergistic effect in one or more of decreasing inflammation, decreasing catabolism, and increasing anabolism.

2. The joint care composition of claim 1, wherein the curcuminoid is curcumin.

3. A pet food product comprising the joint care composition of claim 1 in an effective amount.

4. The pet food product of claim 3, further comprising a crude protein, a fat, and a carbohydrate.

5. The pet food product of claim 3, wherein the composition includes about 5% to 15% moisture.

6. The pet food product of claim 3, wherein the composition includes about 15% to 70% moisture.

7. The pet food product of claim 3, wherein the composition includes about 70% to 90% moisture.

8. The pet food product of claim 3, wherein the composition treats osteoarthritis in a mammal.

9. The pet food product of claim 3, wherein the pet food product includes, on a dry matter basis, from 0.005 wt % to 1.1 wt % curcuminoid, from 0.1 wt % to 1.1 wt % green tea polyphenol, and from 0.5 wt % to 5 wt % hydrolyzed collagen.

10. The pet food product of claim 3, wherein the curcuminoid is curcumin.

11. The pet food product of claim 3, wherein the green tea polyphenol is epigallocatechin gallate.

12. The pet food product of claim 3, further comprising at least one of piperine, bromelain, or one or more phospholipids.

13. The pet food product of claim 12, wherein the phospholipid comprises phosphatidylcholine.

14. The pet food product of claim 13, wherein the phospholipid comprises lecithin.

15. A joint care composition consisting of curcuminoid, green tea polyphenol, and hydrolyzed collagen, wherein the combination of curcuminoid, green tea polyphenol, and hydrolyzed collagen provides a synergistic effect in one or more of decreasing inflammation, decreasing catabolism, and increasing anabolism.

16. The joint care composition of claim 15, wherein the green tea polyphenol is epigallocatechin gallate.

* * * * *